United States Patent [19]

Morino et al.

[11] Patent Number: 5,306,496

[45] Date of Patent: Apr. 26, 1994

[54] ANTIBIOTICS NK374186A, NK374186B, NK374186B3 AND NK374186C3, PROCESS FOR PRODUCING THE SAME, AND USE OF THE SAME

[75] Inventors: Tomio Morino, Omiya; Masakazu Nishimoto, Yono; Mituyuki Nishide, Yono; Akira Masuda, Yono; Masatoshi Yamada, Yono; Eiji Kawano, Higashimurayama; Takaaki Nishikiori, Yono; Seiichi Saito, Kashiwa, all of Japan

[73] Assignee: Nippon Kayaku Kabushiki Kaisha, Tokyo, Japan

[21] Appl. No.: 896,676

[22] Filed: Jun. 10, 1992

[30] Foreign Application Priority Data

Jul. 10, 1991 [JP] Japan ................................. 3-195123

[51] Int. Cl.$^5$ ......................... A61K 35/70; C12P 1/02
[52] U.S. Cl. ................... 424/117; 424/122; 435/171
[58] Field of Search ................. 424/117, 122; 435/171

Primary Examiner—Jerome D. Goldberg
Attorney, Agent, or Firm—Nields & Lemack

[57] ABSTRACT

Novel antibiotics NK374186A, NK374186B, NK374186B3 and NK374186C3 having antibacterial, antineoplastic, immunomodulation, and liver regeneration promoting activities are provided.

NK374186A, NK374186B, NK374186B3 and NK374186C3 are obtained by culturing NK374186 strain (FERM P-12285) (FERM-BP 3870) belonging to the genus Penicillium. NK374186A is a compound represented by a rational formula of $C_{34}H_{61}N_3O_{12}S_9$ and having a molecular weight of M+ 735 (FD-MS m/z); NK374186B is a compound represented by a rational formula of $C_{34}H_{61}N_3O_9$ and having a molecular weight of M+ 655 (FD-MS m/z); NK374186B3 is a compound represented by a rational formula of $C_{34}H_{61}N_3O_9$ and having a molecular weight of M+ 655 (FD-MS m/z); and NK374186C3 is a compound represented by a rational formula of $C_{32}H_{59}N_3O_7$ and having a molecular weight of M+ 597 (FD-MS m/z).

5 Claims, 16 Drawing Sheets

5,306,496

ANTIBIOTICS NK374186A, NK374186B, NK374186B3 AND NK374186C3, PROCESS FOR PRODUCING THE SAME, AND USE OF THE SAME

BACKGROUND OF THE INVENTION

Examples of known antineoplastics include adriamycin, bleomycin, cisplatin and etoposide.

However they are highly toxic, which makes them unsatisfactory. On the other hand, none of the existing immunomodulators or remedies for hepatic diseases can give satisfactory effects either. It has been therefore urgently required to invent novel compounds suitable for these purposes.

SUMMARY OF THE INVENTION

Under these circumstances, the present inventors have examined a number of microbial metabolites and, as a result, have found out that a mold strain can produce antibiotics NK374186A, NK374186B, NK374186B3 and NK374186C3 each having a weak activity of suppressing the growth of mammalian cells.

The present invention has been completed based on the above-mentioned finding.

Accordingly, the present invention relates to novel antibiotics NK374186A, NK374186B, NK374186B3 and NK374186C3.

Each of the compounds of the present invention has an antibacterial activity and is therefore usable as a bactericide. In addition, it is expected to be useful as an antineoplastic, since it has an activity of suppressing cancer cell growth. Therefore, the present invention relates to a bactericide or an antineoplastic which comprises at least an antibiotic selected from the group consisting of NK374186A, NK374186B, NK374186B3 and NK374186C3 as an active ingredient.

The compounds of the present invention, in particular, NK374186A and NK374186B have immunomodulation effects and the administration of an effective dose of these compounds to warm-blooded animals, including man, can exert immunomodulation, in particular, immunopotentiation effects on these animals. Therefore, these compounds are useful as an immunomodulator especially, immunopotentiator.

When an effective dose of the compound of the present invention, in particular, NK374186A is administered to warm-blooded animals including man, it exerts a liver regeneration promoting effect so as to promote the regeneration of the damaged liver suffering from, for example, partial excision. Accordingly, it is expected that this compound may be useful as a liver regeneration promoter.

DETAILED DESCRIPTION OF THE INVENTION

Figure 1:
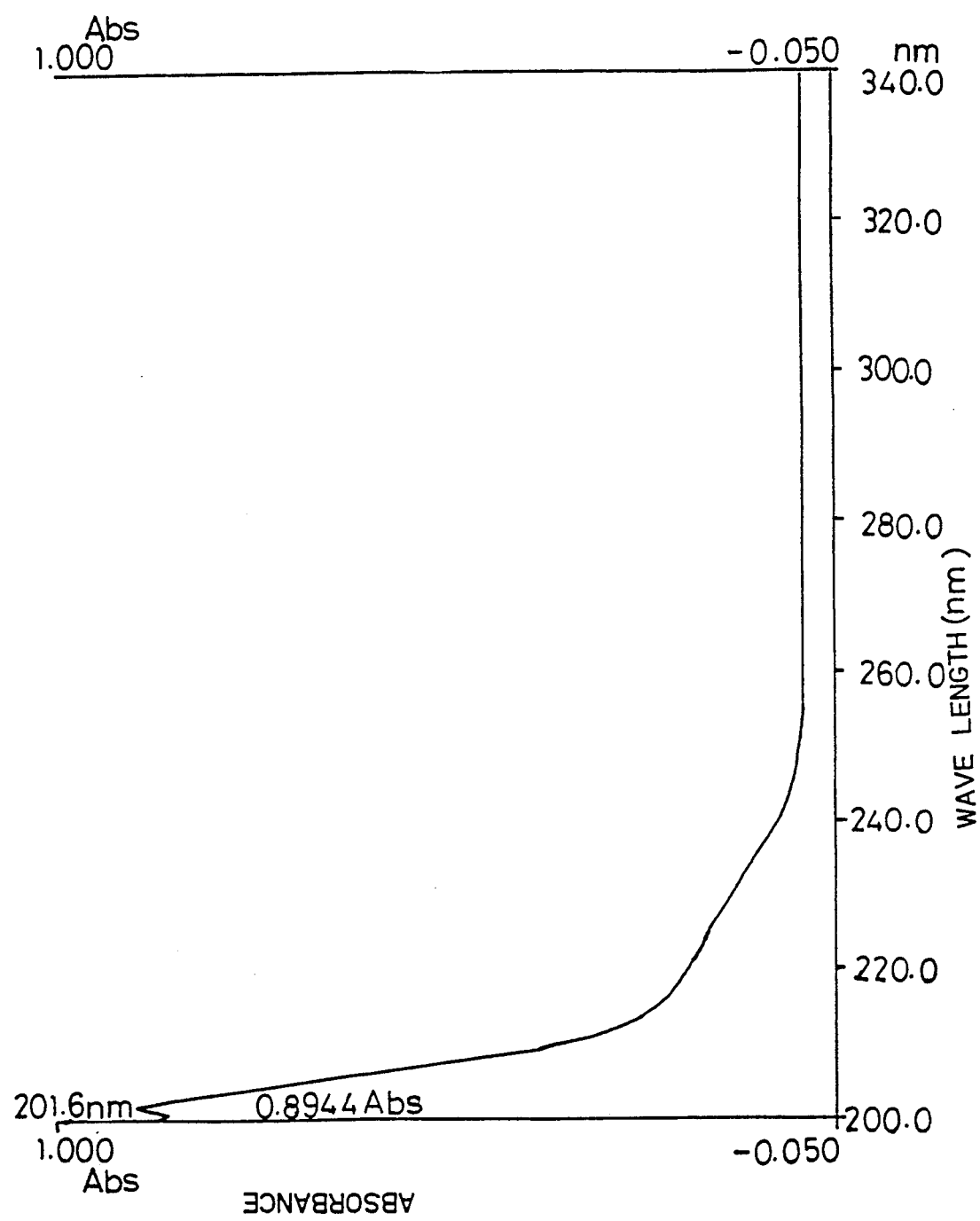
FIG. 1 is an UV absorption spectrum of NK374186A.

The above-mentioned novel antibiotics NK374186A, NK374186B, NK374186B3 and NK374186C3 can be obtained by culturing NK374186A-, NK374186B-, NK374186B3- and NK374186C3- producing strains belonging to the genus Penicillium and collecting the antibiotics NK374186A, NK374186B, NK374186B3 and NK374186C3 thus accumulated from the culture medium.

As a typical example of the strains capable of producing NK374186A, NK374186B, NK374186B3 and NK374186C3, a strain NK374816 isolated from soil of a copse in Yahiko, Niigata in April, 1989 which has been deposited with Fermentation Research Institute under the accession number FERMP-12285 (hereinafter referred to simply as NK374186 strain) (FERM-BP3870) may be cited.

The mycological properties of the NK374186 strain are as follows.

It grows well on a malt extract agar medium at 27° C. The diameter of a colony reaches 54.3 mm after culturing the strain for 10 days. Aerial hyphae are formed on the surface of the colony. As the culture proceeds, the center of the colony turns from yellow into pink and then gray green. On the other hand, the reverse face of the colony turns from pale yellow into yellow, pink and then red.

It grows well in a potato/glucose agar medium at 27° C. and the diameter of a colony reaches 53.0 mm after culturing for 10 days. Color changes similar to those observed in the case of the culture in the malt extract medium are observed.

In Czapek's medium at 27° C., this strain does not grow well and the diameter of a colony reaches 22.3 mm after culturing for 10 days. As the culture proceeds, both of the surface and reverse face of the colony turn from pink to red at the center. Different from the above-mentioned two media, however, the surface does not turn gray green.

It grows well in a YpSs agar medium at 27° C. and the diameter of a colony reaches 43.6 mm after culturing for 10 days.

On the YpSs agar medium, this NK374186 strain forms a number of linked ellipsoidal or subspherical (about 2 µm) conidiospores with rough surfaces. Several (3 to 5) phialides (about 1.5 µm × 8 µm) of a sharpened form, just like a pen point, form a whorl. Several (4 to 8) metulae (about 2 μm×8 μm) grow in crowds. The temperature suitable for the growth of this strain ranges from 10° to 37° C. and the optimum temperature is around 28° C. The pH value suitable for the growth thereof ranges from 2 to 11 and the optimum pH value is from 4 to 8.

Based on the above-mentioned mycological properties, it is revealed that this strain belongs to the genus Penicillium of phialo type, Hyphomycetes, Deuteromycotina, Eumypetes, in accordance with Genus Penicillium & Its Teleomorphic States; Eupenicillium & Talaromyces (John I. Pitt, Academic Press, 1979). Thus this strain is named *Penicillium sp.* NK374186 strain.

Similar to other strains of the genus Penicillium, the strain belonging to the genus Penicillium to be used in the present invention is highly labile. Therefore it can be easily mutated by artificial mutagenic procedures with the use of, for example, UV light, X-ray or chemicals. Any mutant is usable in the present invention so long as it can produce the physiologically active substance NK374186A, NK374186B, NK374186B3 or NK374186C3, namely, the subject of the present invention. These substances will be hereinafter referred to simply as NK374186.

In order to produce NK374186 in accordance with the present invention, the above-mentioned strain is cultured in a medium containing nutrients utilizable for molds under aerobic conditions. As the nutrition sources, those conventionally utilized for culturing molds are available. For example, a carbon source may be selected from among glucose, fructose, glycerol, sucrose, dextrin, galactose, organic acids and mixtures thereof.

Inorganic and organic nitrogen sources may be selected from among ammonium chloride, ammonium sulfate, urea, ammonium nitrate, sodium nitrate, peptone, meat extract, yeast extract, dry yeast, corn steep liquor, soybean flour, cotton seed oil cake, casamino acids, bactosoytone, soluble vegetable protein, oat meal and mixtures thereof.

In addition, the medium may contain inorganic salts such as common salt, calcium carbonate, magnesium sulfate, copper sulfate, iron sulfate, zinc sulfate, manganese chloride or phosphates, if needed. Furthermore, organic substances such as amino acids, vitamins or nucleic acids and inorganic substances may be optionally added thereto.

The strain may be cultured by liquid culture, in particular, submerged spinner culture. The culture may be preferably carried out at a temperature of from 15° to 35° C. and at a neutral or slightly acidic pH value.

In the case of liquid culture, the products NK374186A, B, B3 and C3 are formed and accumulated in the culture medium within 3 to 5 days, usually. When the amount of the product in the cells reaches the maximum level, the culture is ceased and the cells are separated from the culture medium by filtering, followed by the isolation and purification of each product.

Each product of NK374186A, B, B3 and C3 may be isolated and purified from the cells by a procedure commonly employed for isolating a microbial metabolite from cultured cells.

More specifically, the culture medium is separated into a filtrate and the cells by a conventional filtration procedure. Next, the cells are extracted with methanol and the same amount of water is added to the extract thus obtained. Then the target substance is adsorbed by a resin HP-20. After washing, the resin is eluted with 60% acetone and methanol to thereby give fractions 1 and 2. The fraction 1 is then concentrated to dryness and successively subjected to silica gel column chromatography and LH-20 column chromatography, as will be described in the following Example. Active fractions are combined and concentrated under reduced pressure. Thus NK374186A is obtained as a colorless product.

On the other hand, the fraction 2 is concentrated to dryness and subjected to silica gel chromatography, as will be described in the following Example. Thus three active fractions 2a, 2b and 2c are obtained. The fractions 2a and 2b are subjected to LH-20 chromatography and thus colorless products NK374186B and NK374186B3 are respectively obtained. The fraction 2c is successively subjected to silica gel column chromatography and LH-20 column chromatography to thereby give NK374186C3.

Figure 2:
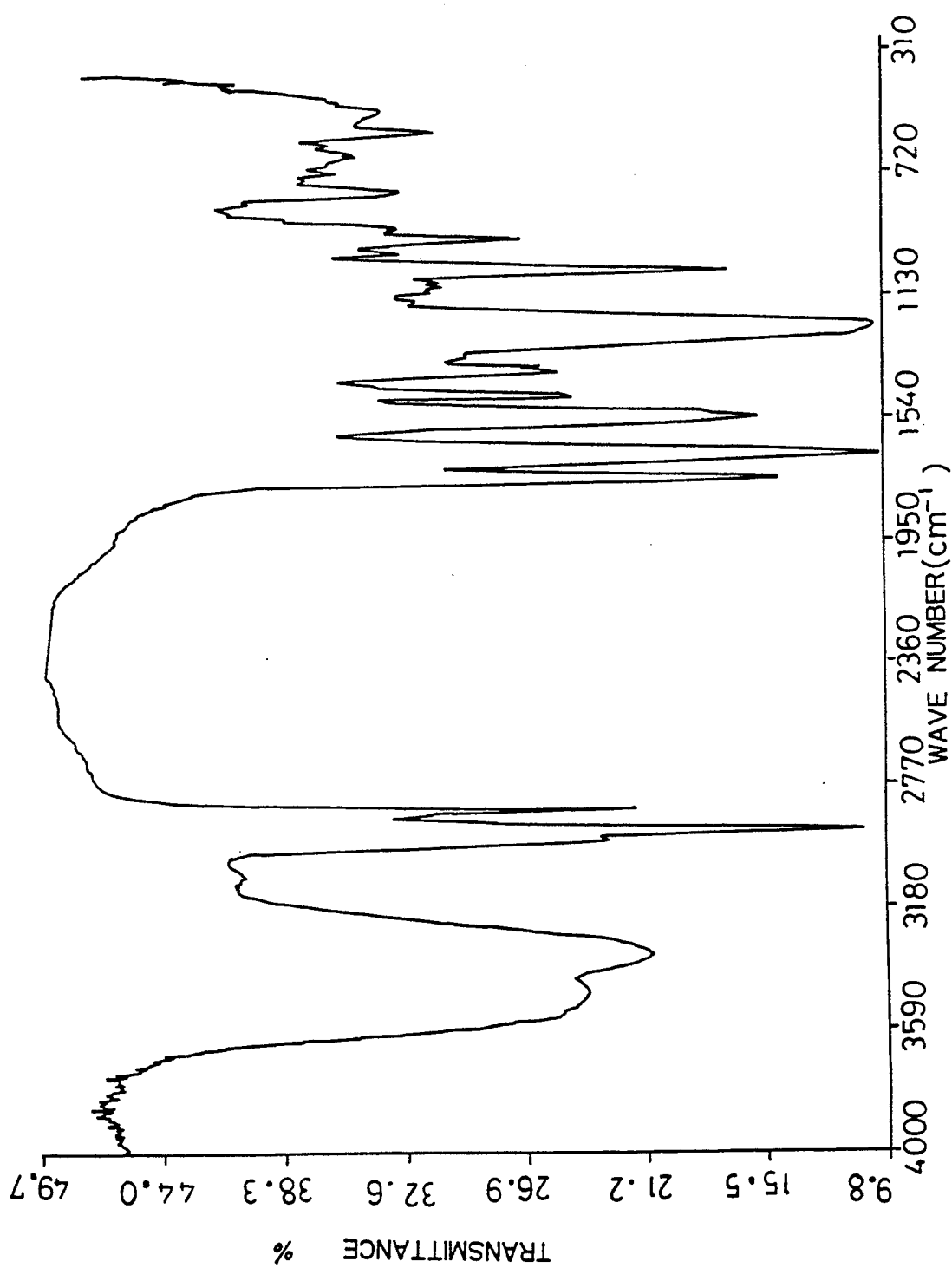
FIG. 2 is an IR absorption spectrum of NK374186A determined by using a potassium bromide tablet.
Figure 3:
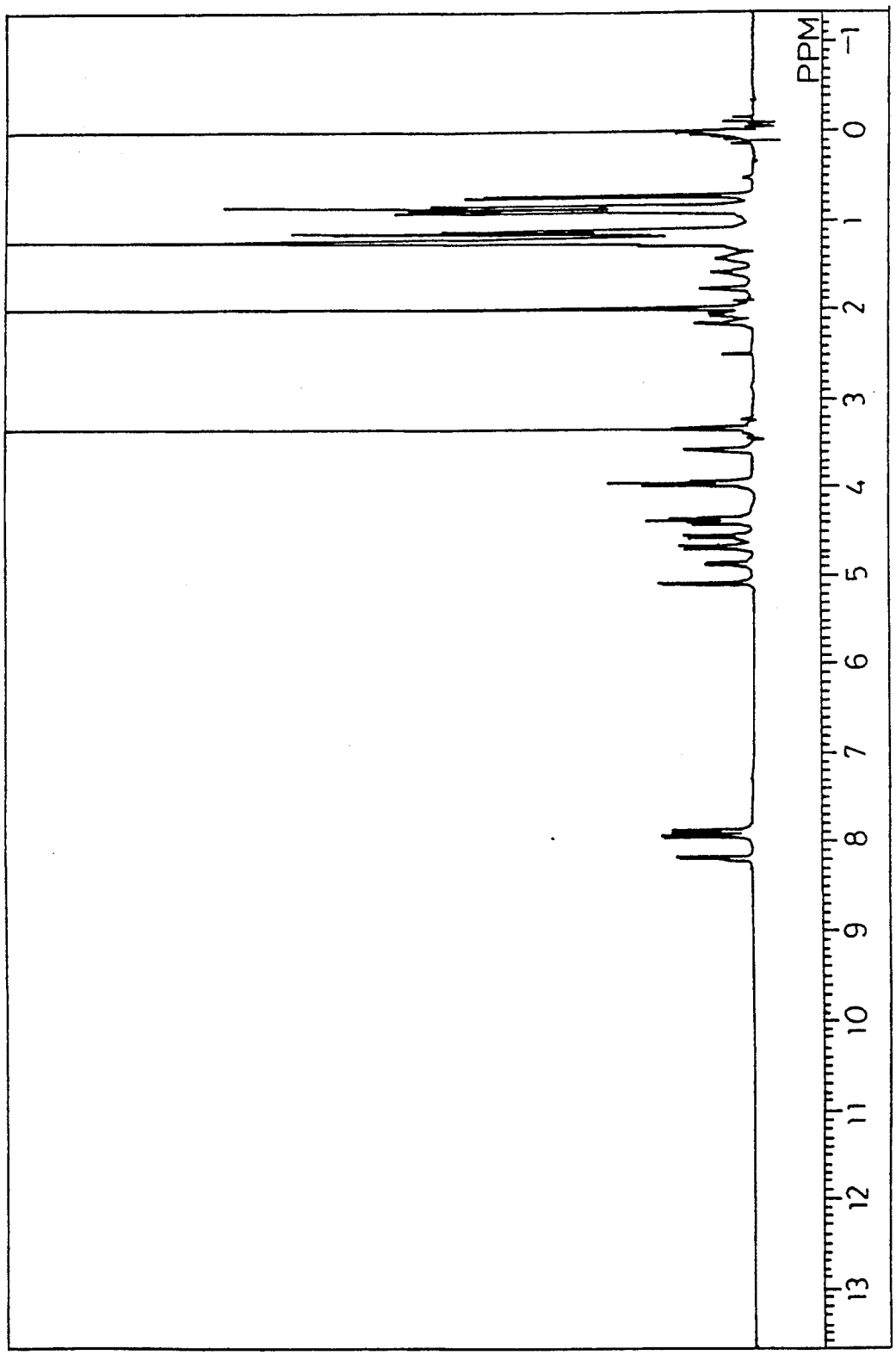
FIG. 3 is a proton NMR spectrum of NK374186A determined in heavy dimethyl sulfoxide.
Figure 4:
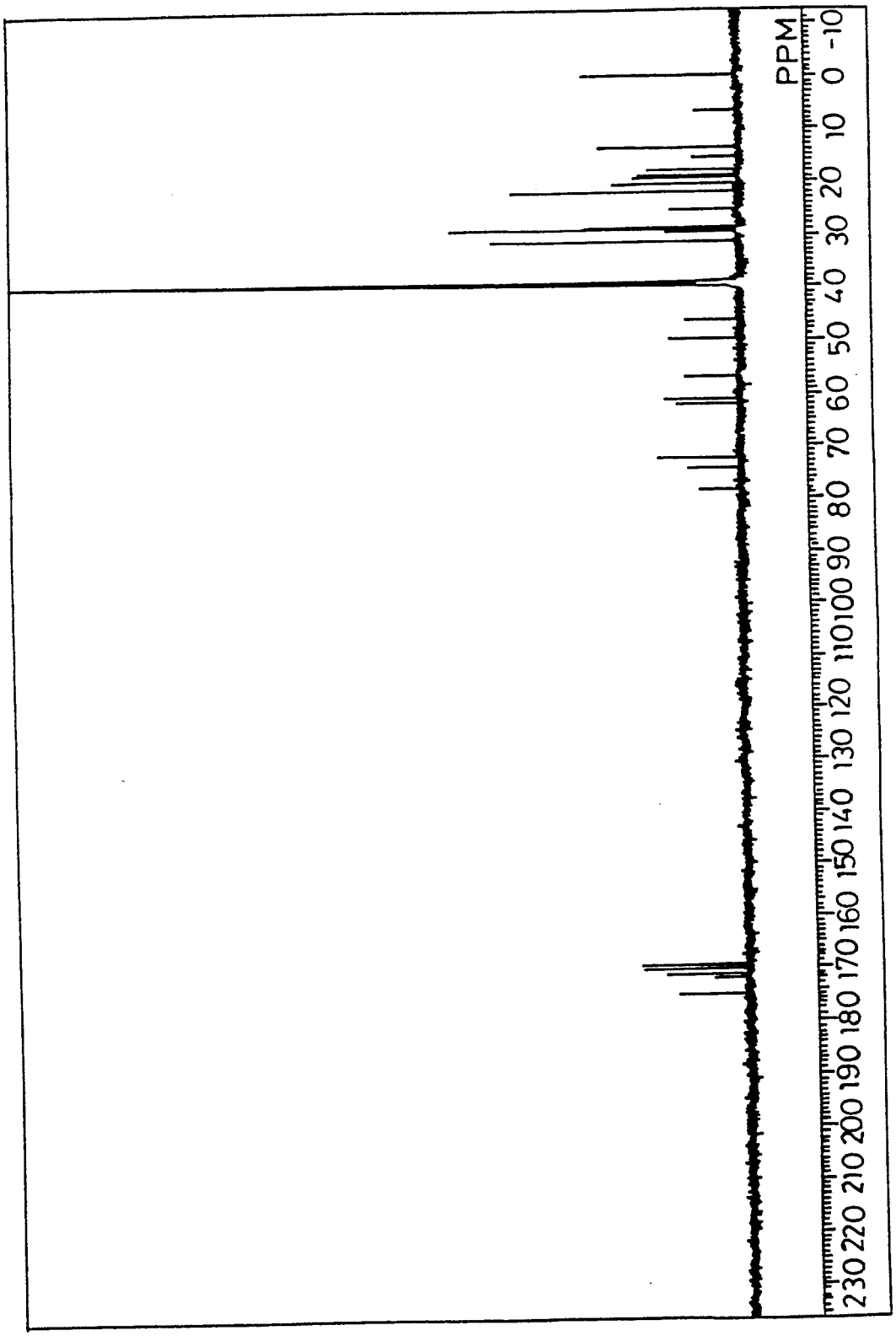
FIG. 4 is a carbon NMR spectrum of NK374186A determined in heavy dimethyl sulfoxide.
Figure 5:
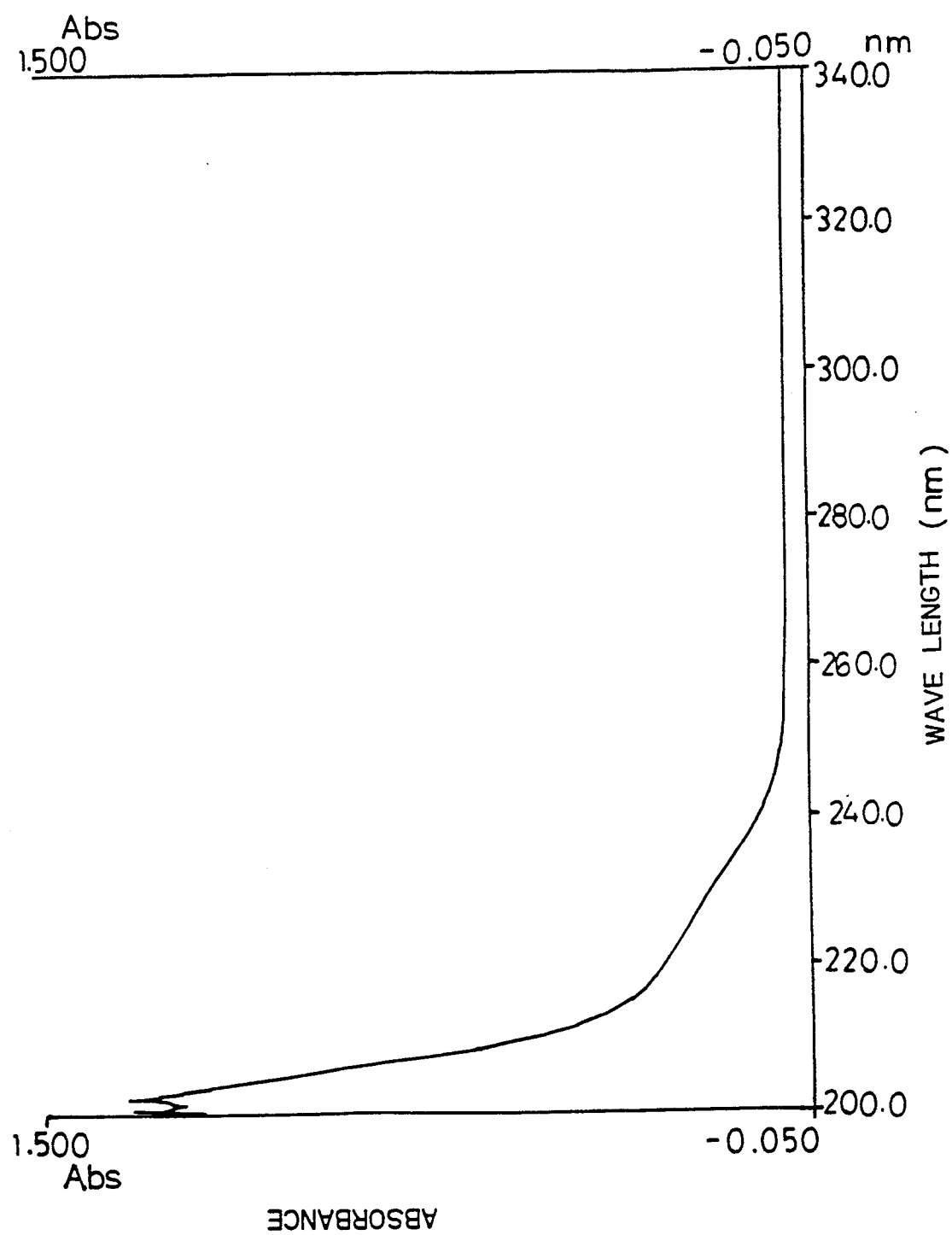
FIG. 5 is an UV absorption spectrum of NK374186B.
Figure 6:
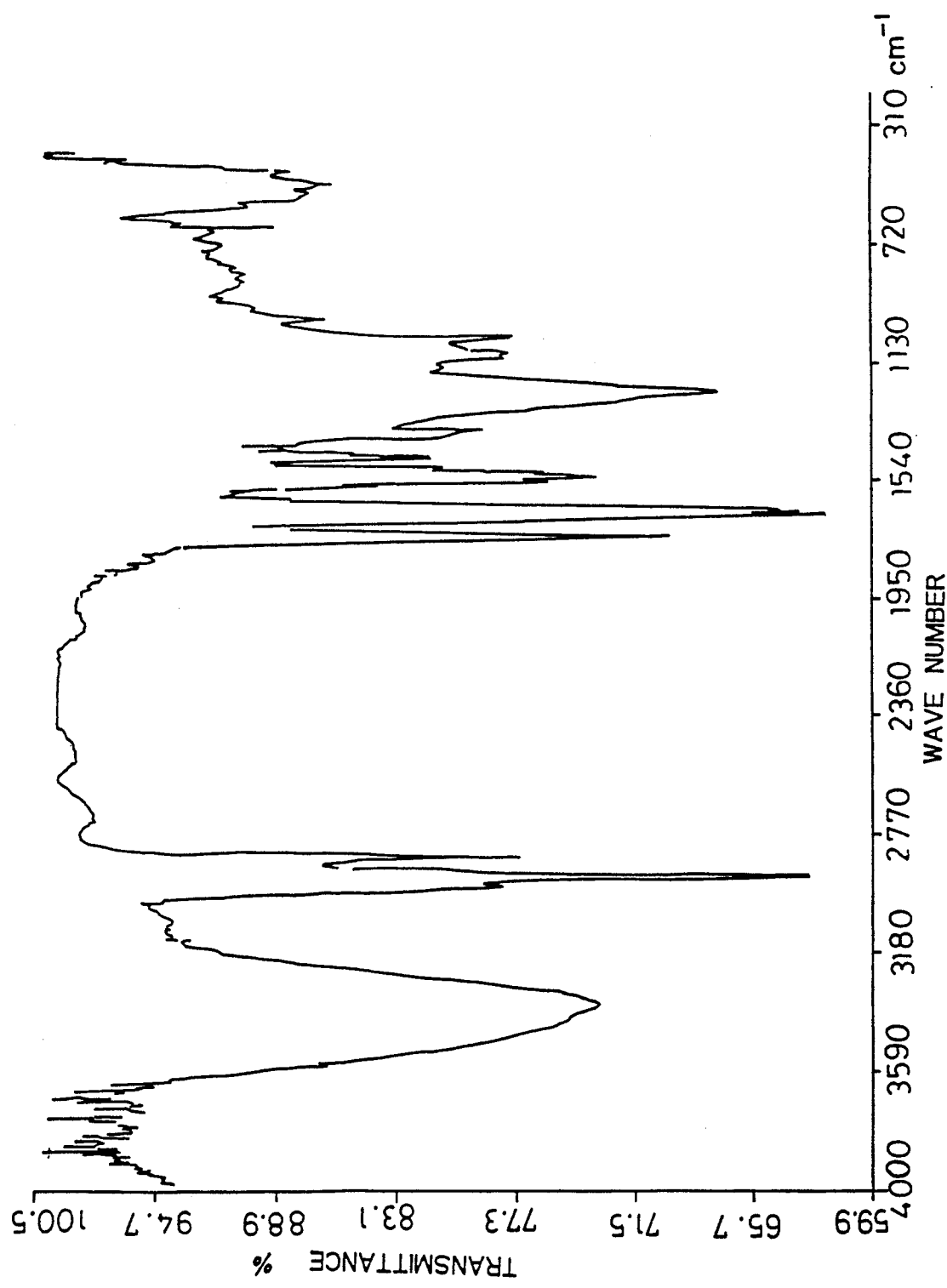
FIG. 6 is an IR absorption spectrum of NK374186B determined by using a potassium bromide tablet.
Figure 7:
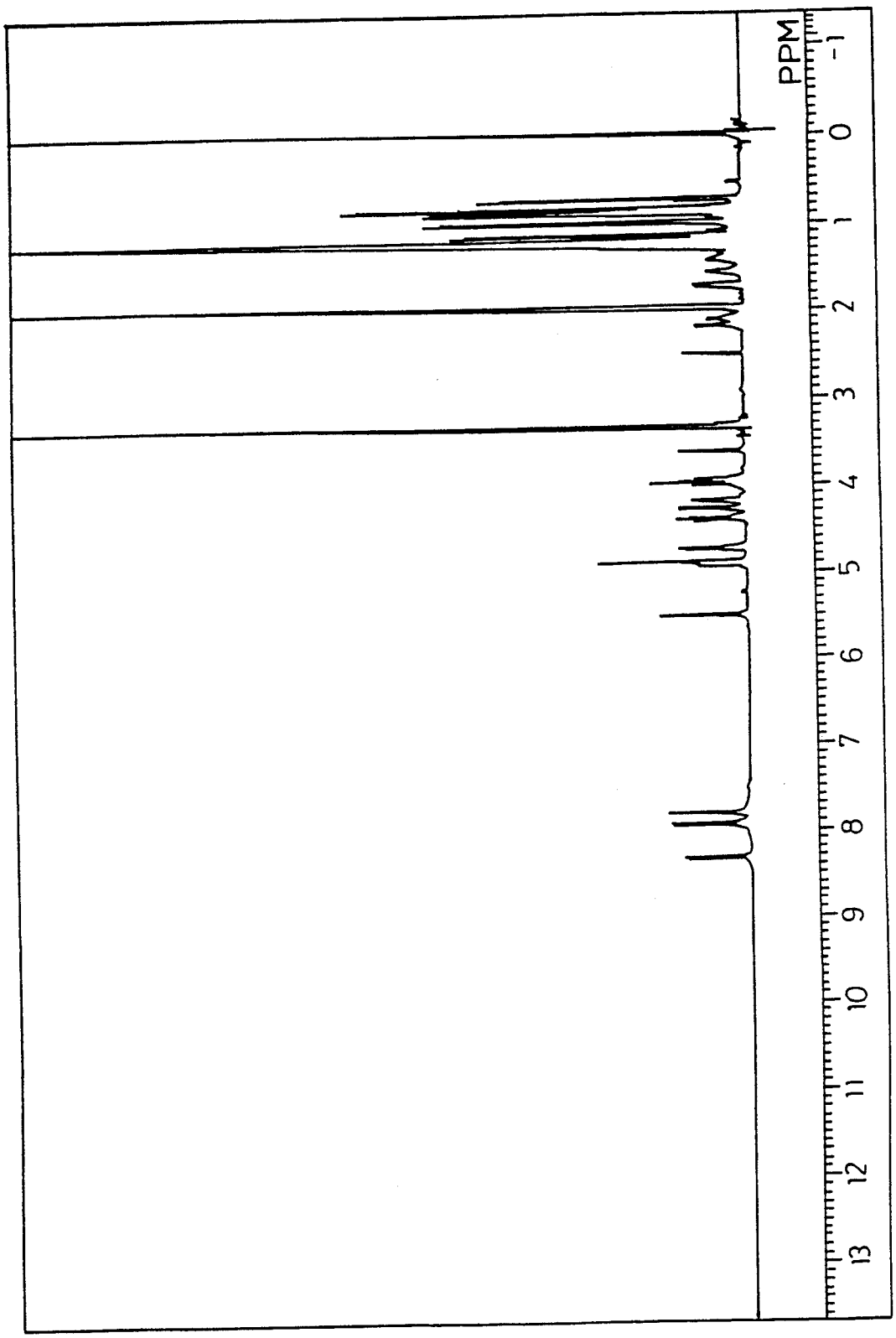
FIG. 7 is a proton NMR spectrum of NK374186B determined in heavy dimethyl sulfoxide.
Figure 8:
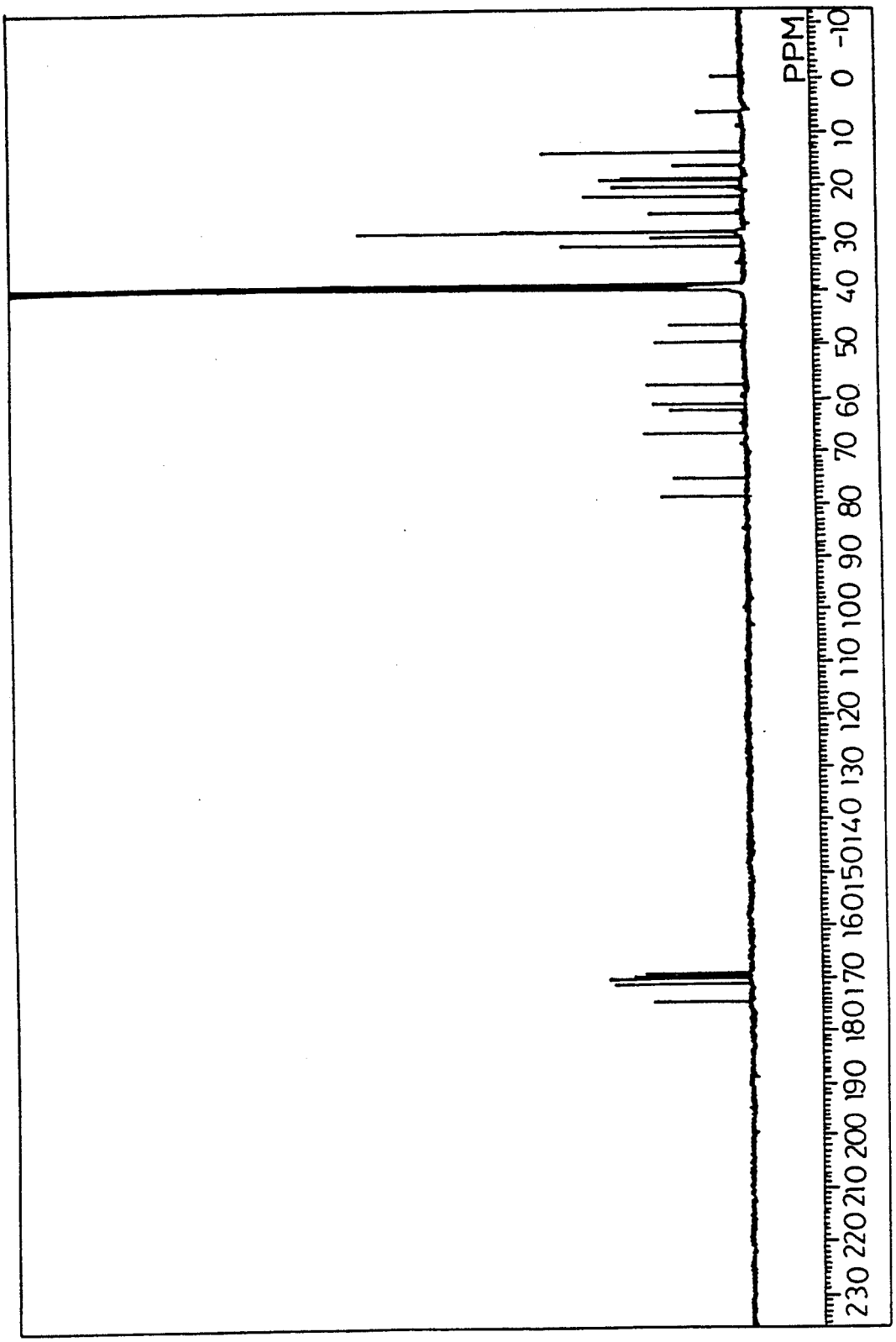
FIG. 8 is a carbon NMR spectrum of NK374186B determined in heavy dimethyl sulfoxide.
Figure 9:
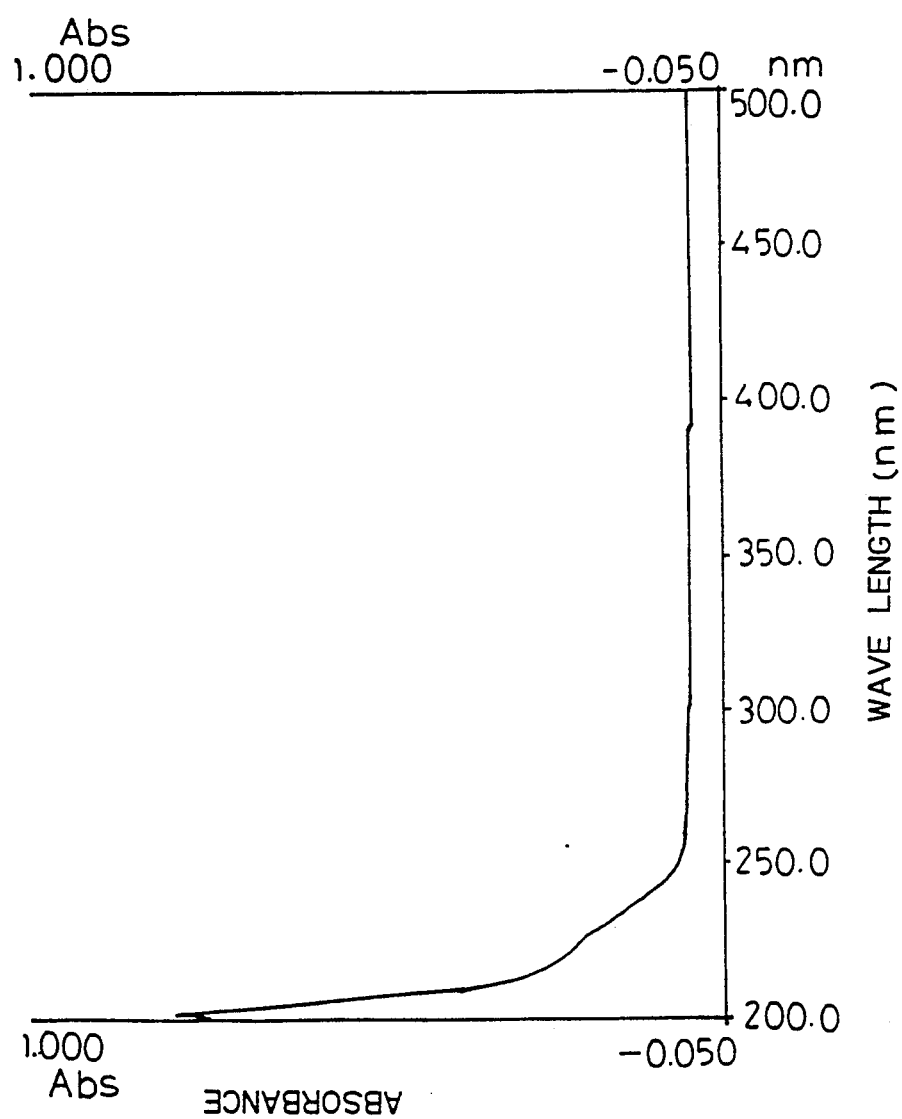
FIG. 9 is an UV absorption spectrum of NK374186B3.
Figure 10:
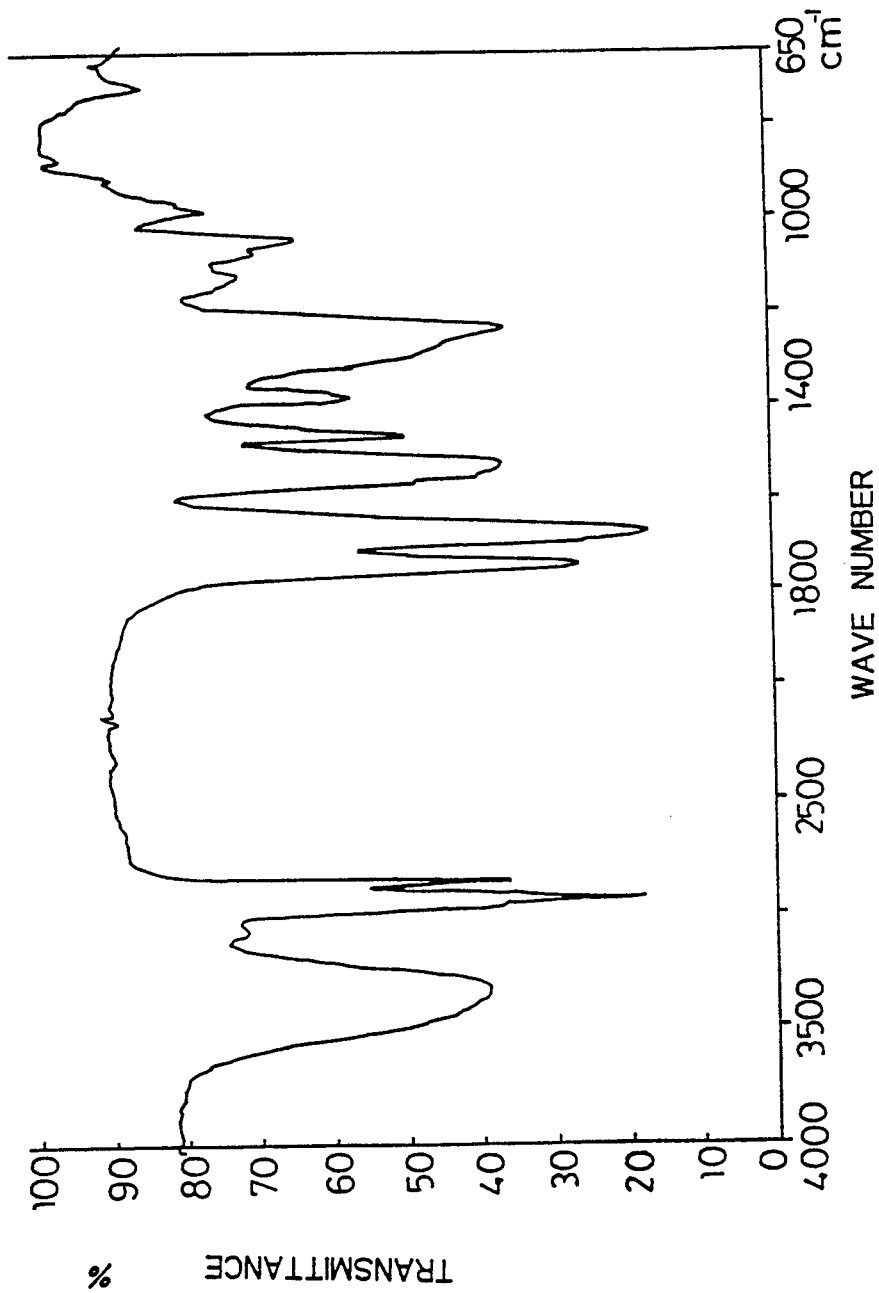
FIG. 10 is an IR absorption spectrum of NK374186B3 determined by using a potassium bromide tablet.
Figure 11:
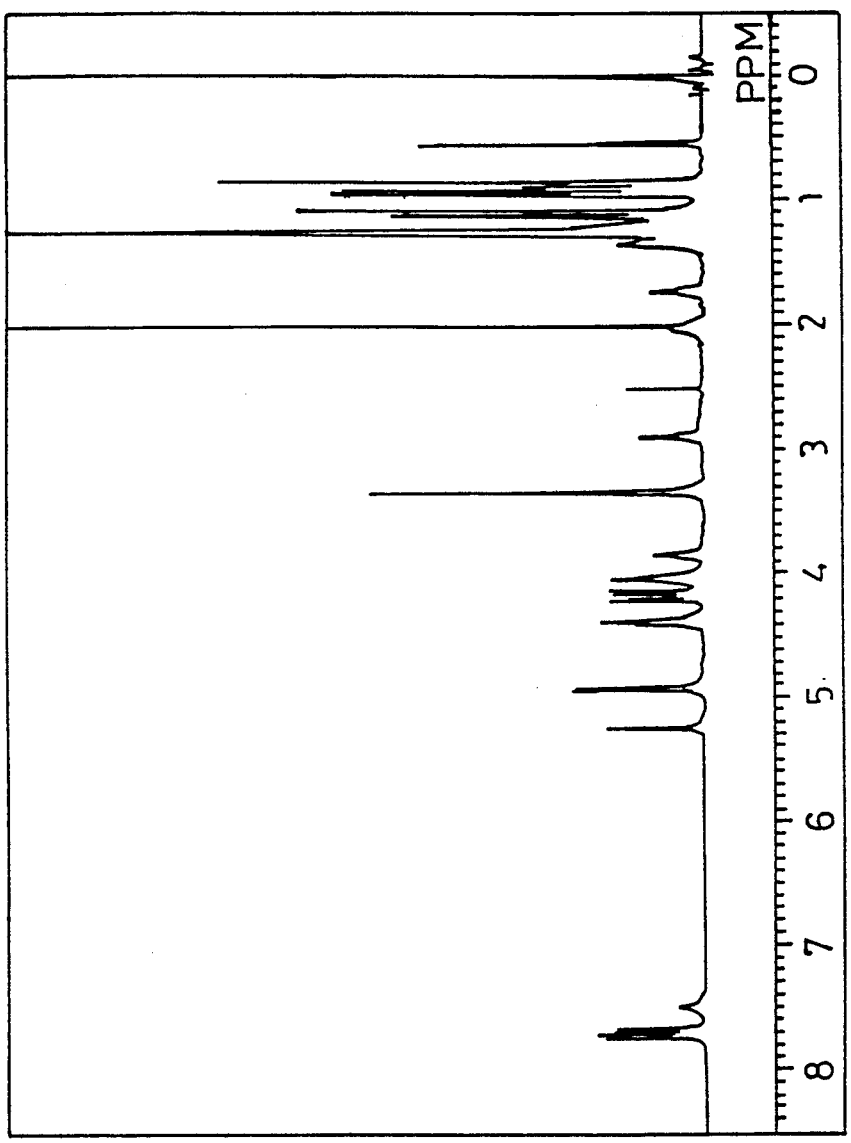
FIG. 11 is a proton NMR spectrum of NK374186B3 determined in heavy dimethyl sulfoxide.
Figure 12:
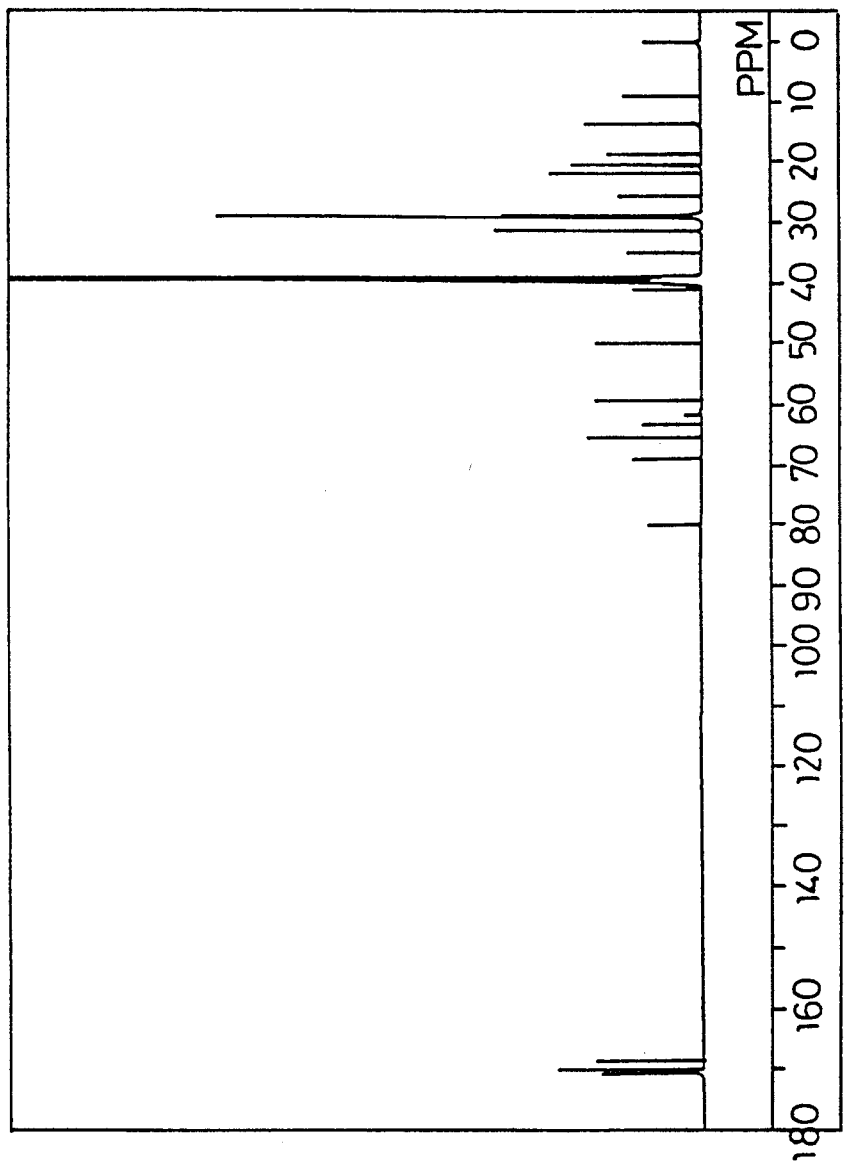
FIG. 12 is a carbon NMR spectrum of NK374186B3 determined in heavy dimethyl sulfoxide.
Figure 13:
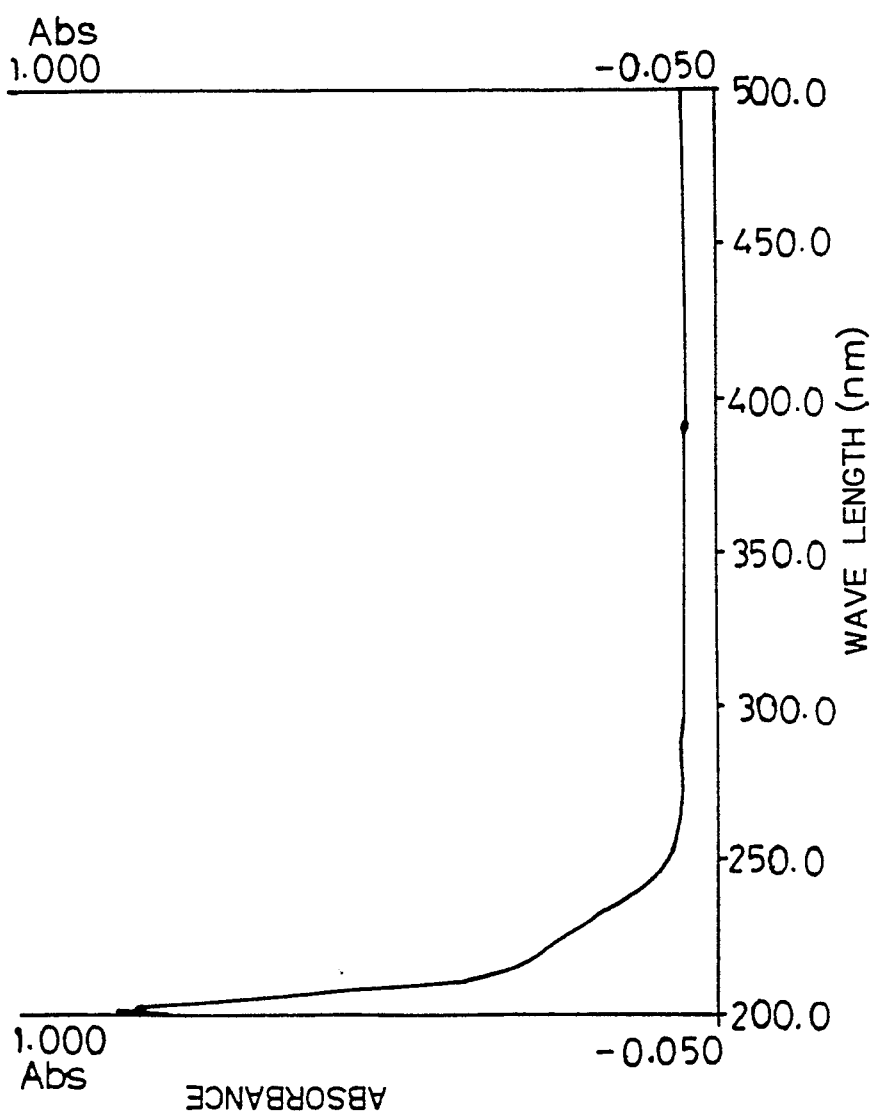
FIG. 13 is an UV absorption spectrum of NK374186C3.
Figure 14:
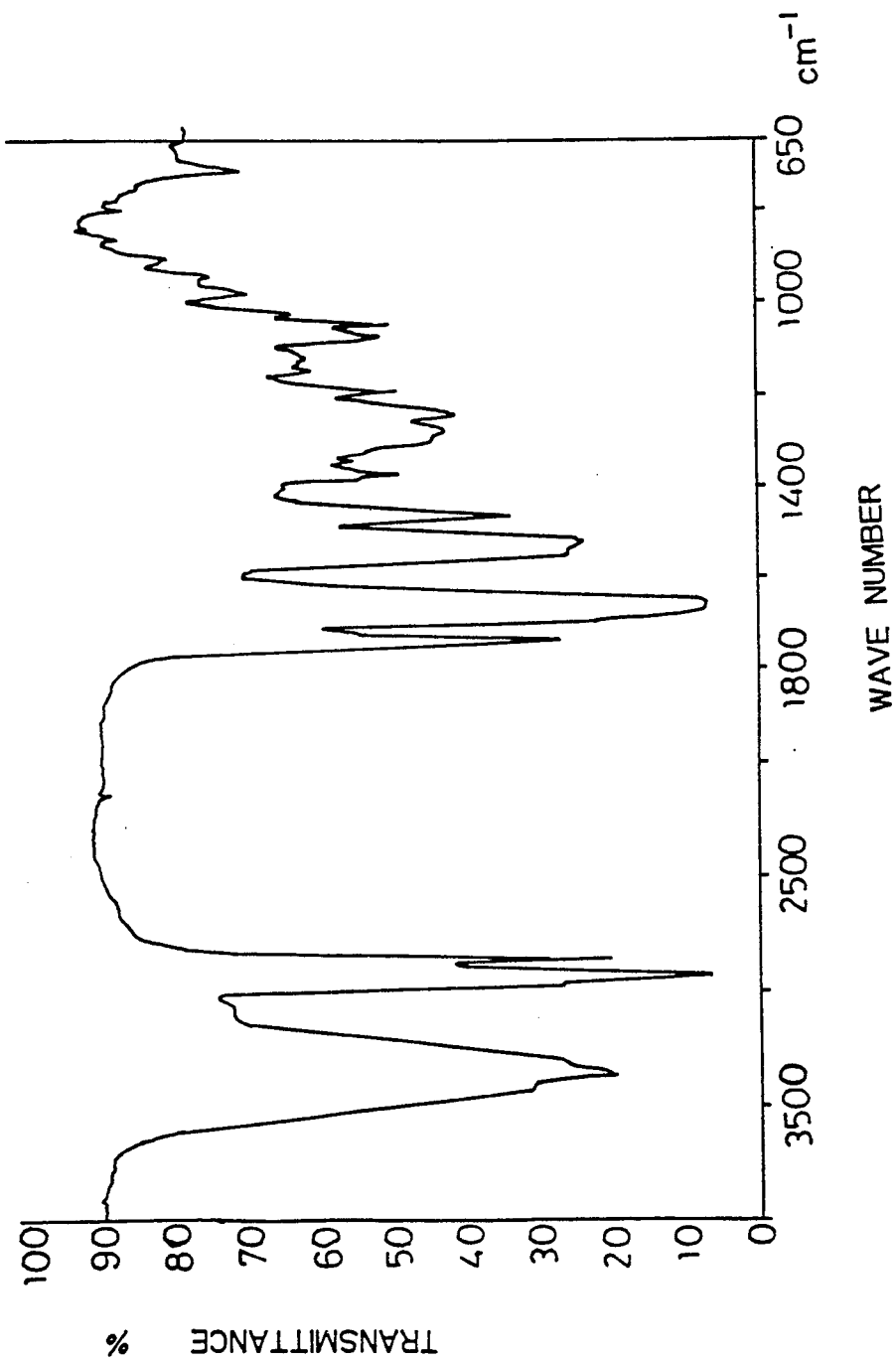
FIG. 14 is an IR absorption spectrum of NK374186C3 determined by using a potassium bromide tablet.
Figure 15:
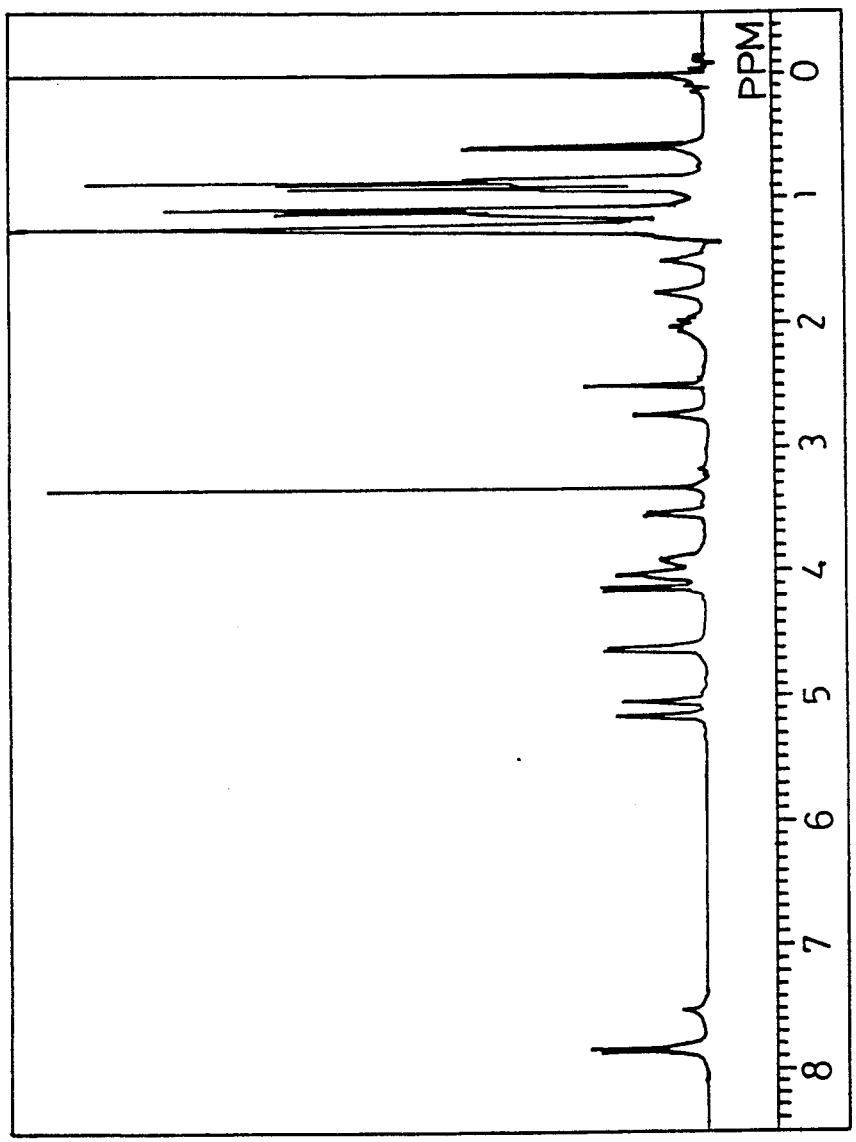
FIG. 15 is a proton NMR spectrum of NK374186C3 determined in heavy dimethyl sulfoxide.
Figure 16:
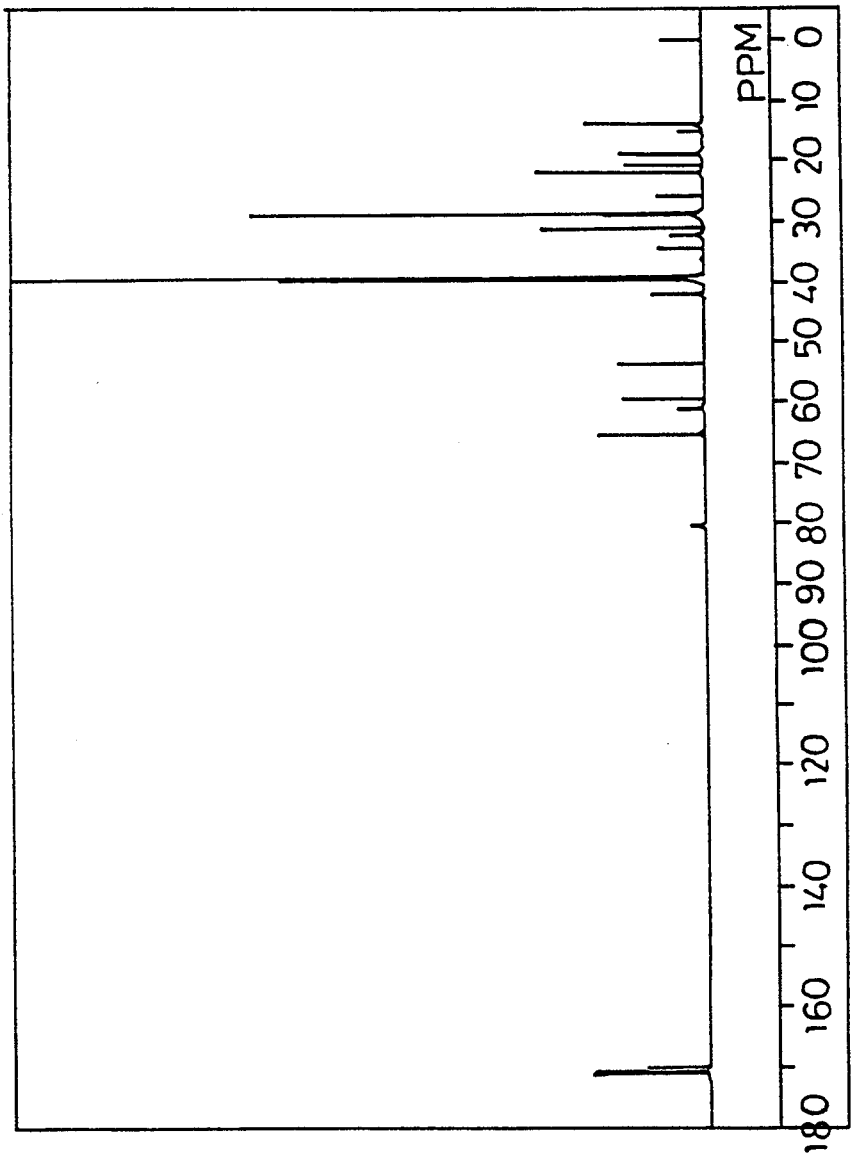
FIG. 16 is a carbon NMR spectrum of NK374186C3 determined in heavy dimethyl sulfoxide.

The physicochemical properties of the antibiotics NK374186A, NK374186B, NK374186B3 and NK374186C3 thus obtained or salts thereof are as follows:

a) NK374186A
1) appearance: colorless powder,
2) molecular weight: FD-MS m/z (M+ 735),
3) rational formula: $C_{34}H_{61}N_3O_{12}S$,
4) solubility: soluble in lower alcohols, chloroform and ethyl acetate,
5) Rf value in silica gel thin layer (Art.5715, a product of Merck) chromatography: 0.12 with the use of a chloroform/methanol mixture (20:1) as developer,
6) UV absorption spectrum: refer to FIG. 1,
7) IR absorption spectrum: refer to FIG. 2 (determined by using potassium bromide tablet),
8) proton NMR spectrum: refer to FIG. 3 (determined in heavy DMSO),
9) carbon NMR spectrum: refer to FIG. 4 (determined in heavy DMSO), and
10) color reaction: positive in phosphomolybdic acid/sulfuric acid reaction and Tolidine-Chlorine reaction and negative in ninhydrin reaction;

b) NK374186B
1) appearance: colorless powder,
2) molecular weight: FD-MS m/z (M+ 655),
3) rational formula: $C_{34}H_{61}N_3O_9$,
4) solubility: soluble in lower alcohols, chloroform and ethyl acetate,
5) Rf value in silica gel thin layer (Art.5715, a product of Merck) chromatography: 0.35 with the use of a chloroform/methanol mixture (20:1) as developer,
6) UV absorption spectrum: refer to FIG. 5,
7) IR absorption spectrum: refer to FIG. 6 (determined by using potassium bromide tablet),
8) proton NMR spectrum: refer to FIG. 7 (determined in heavy DMSO),
9) carbon NMR spectrum: refer to FIG. 8 (determined in heavy DMSO), and
10) color reaction: positive in phosphomolybdic acid/sulfuric acid reaction and Tolidine-Chlorine reaction and negative in ninhydrin reaction;

c) NK374186B3
1) appearance: colorless powder,
2) molecular weight: FD-MS m/z (M+655),
3) rational formula: $C_{34}H_{61}N_3O_9$, 4) solubility: soluble in lower alcohols, chloroform and ethyl acetate,
5) Rf value in silica gel thin layer chromatography: 0.49 with the use of a chloroform/methanol mixture (20:1) as developer,
6) UV absorption spectrum: refer to FIG. 9,
7) IR absorption spectrum: refer to FIG. 10 (determined by using potassium bromide tablet),
8) proton NMR spectrum: refer to FIG. 11 (determined in heavy DMSO),
9) carbon NMR spectrum: refer to FIG. 12 (determined in heavy DMSO), and
10) color reaction: positive in phosphomolybdic acid/sulfuric acid reaction and Tolidine-Chlorine reaction and negative in ninhydrin reaction; and d) NK374186C3
1) appearance: colorless powder,
2) molecular weight: FD-MS m/z (M+ 597),
3) rational formula: $C_{34}H_{59}N_3O_7$,
4) solubility: soluble in lower alcohols, chloroform and ethyl acetate,
5) Rf value in silica gel thin layer chromatography: 0.33 with the use of a chloroform/methanol mixture (20:1) as developer,
6) UV absorption spectrum: refer to FIG. 13,
7) IR absorption spectrum: refer to FIG. 14,
8) proton NMR spectrum: refer to FIG. 15 (determined in heavy DMSO),
9) carbon NMR spectrum: refer to FIG. 16 (determined in heavy DMSO), and
10) color reaction: positive in phosphomolybdic acid/sulfuric acid reaction and Tolidine-Chlorine reaction and negative in ninhydrin reaction.

As will be described hereinafter, it is expected that the NK374186 of the present invention is useful as a drug such as an antibacterial agent, an antineoplastic, an immunomodulator or a liver regeneration promoter.

When the compound of the present invention is to be used as a drug, it may be formulated and administered by various methods conventionally known in the art. Namely, it may be given via, for example, injection, oral administration or rectal administration. It may be formulated into, for example, injections, dusts, granules, tablets or suppositories.

In the formulation of NK374186A, B, $B_3$ or $C_3$, pharmacological adjuvants commonly employed in the art, for example, carriers, and other auxiliaries such as stabilizers, preservatives, soothing agents or emulsifiers may be employed if needed, so long as the effects of NK374186 are not deteriorated thereby.

The content of NK374186A, B, $B_3$ or $C_3$ in a pharmaceutical preparation may be widely varied depending on, for example, the formulation state. In general, a preparation comprises from 0.01 to 100% by weight, preferably from 0.1 to 70% by weight, of NK374186A, B, $B_3$ or $C_3$ and the balance of other components such as carriers and other auxiliaries commonly used in medicines.

The dose of NK374186A, B, $B_3$ or $C_3$ may vary depending on, for example, the conditions of a subject. It may be generally administered to an adult in a dose of from 0.01 to 800 mg per day. When the compound is to be repetitively administered, it is desirable to control the daily dose at a lower level.

FUNCTION

1. Antibacterial activity

The antibacterial and antifungal activities of each antibiotic are expressed in minimum inhibitory concentration (MIC) determined by the agar dilution method. In the antibacterial activity test, each test microorganism is inoculated onto a Müller/Hinton medium and cultured therein at 37° C. overnight to observe the growth of the microorganism. In the antifungal activity test, each test microorganism is inoculated onto a Czapek medium and cultured therein at 27° C. for 2 to 3 days, followed by the observation of the growth of the microorganism. Table 1 shows the results.

TABLE 1

| Antibacterial activity of NK374186 A, B, $B_3$ and $C_3$. | | | | |
|---|---|---|---|---|
| | MIC (μg/ml) | | | |
| Organism | A | B | $B_3$ | $C_3$ |
| *Staphylococcus aureus* FDA 209P | >100 | 3.13 | 6.25 | 3.13 |
| *Bacillus subtilis* ATCC 6633 | >100 | >100 | 12.5 | >100 |
| *Bacillus subtilis* IAM 1072 | >100 | 6.25 | not tested | |
| *Bacillus megaterium* ATCC 14945 | >100 | 6.25 | 6.25 | 3.13 |
| *Micrococcus flavus* ATCC 10240 | 12.5 | 3.13 | 3.13 | 3.13 |
| *Mycobacterium luteus* ATCC 9341 | 25.0 | >100 | >100 | >100 |
| *Escherichia coli* NIHJ | >100 | >100 | >100 | >100 |
| *Escherichia coli* K-12 | >100 | >100 | >100 | >100 |
| *Mucor javanicus* IFO 4569 | >100 | >100 | >100 | >100 |
| *Aspergillus niger* IFO 4407 | >100 | >100 | >100 | >100 |
| *Rhizopus hanguchao* IFO 4749 | >100 | >100 | >100 | >100 |
| *Botrytis fabae* IFO 6183 | >100 | >100 | >100 | >100 |
| *Trycophyton mentagrophytes* IFO 5466 | >100 | >100 | >100 | >100 |
| *Candida albicans* IFO 1385 | >100 | >100 | >100 | >100 |
| *Penicillium chrysogenum* IFO 8645 | >100 | >100 | >100 | >100 |

As the above Table 1 clearly shows, the NK374186A of the present invention evidently has an antibacterial activity on *Micrococcus* and *Mycobacterium*. On the other hand, the NK374186B, $B_3$ and $C_3$ of the present invention have a potent antibacterial activity on *Bacilli*, *Staphylococcus* and *Micrococcus*.

2. Cell growth suppressing activity

Cells are incubated in an RPMI 1640 medium containing 10% of fetal calf serum at 37° C. under 5% of $CO_2$. Then these cells are sowed in a 96-well plate and pre-incubated for 1 day, followed by the addition of each test compound. The treatment with the test compound was carried out for 2 days and the activity of suppressing the cell growth was evaluated by the MTT method. Table 2 shows the activities of NK374186 in suppressing the growth of a cancer cell strain Li-7 derived from human hepatic cancer, a cell strain A2780 derived from human ovarian cancer and an adriamycinresistant strain 2780^{4D} obtained from the strain A2780.

TABLE 2

| Compound | Cell growth suppressing activity of NK374186A, B, B₃ and C₃ IC₅₀ [μg/ml] | | |
|---|---|---|---|
| | Li-7 | A2780 | 2780^{4D} |
| A | 40 | 27 | 59 |
| B | 7.0 | 6.6 | 33 |
| B₃ | 3.3 | 1.3 | 4.3 |
| C₃ | 13 | 12 | 14 |

As the above Table 2 clearly shows, the antibiotics NK374186A, NK374186B, NK374186B3 and NK374186C3 suppress the growth of each cell line.

3. Immunomodulation activity of NK374186A and B in lymphoblast formation

An RPMI 1640 medium containing 20% of fetal calf serum, 25 mM of Hepes buffer, 100 μg/ml of streptomycin and 100 U/ml of penicillin G is used. The incubation is carried out in a 96-well flat-bottomed microplate (COSTAR). As a mitogen, lipopolysaccharide (LPS) and concanavalin A (Con A) are used respectively at final concentrations of 100 μg/ml and 5 μg/ml.

The spleen of a BALB/C mouse (female, >20 weeks in age) is taken out and a single-cell suspension is prepared. After removing erythrocytes by hyper shock, the suspension is used as such for the treatment with LPS. For the treatment with Con A, on the other hand, the suspension is passed through a Nylon Fiber (a product of Wako Pure Chemicals, Inc.) for separating T cells. $2 \times 10^5$/well of the spleen cells and each test compound of the concentration as specified above are added to thereby give a total volume of 0.2 ml/well, followed by incubation for 72 hours. 8 hours before the completion of the incubation, 37 KBq/well of [³H]-thymidine is added and the thymidine uptake in the cells is measured. The effect is evaluated based on the ratio of the [³H]-thymidine uptake of a test group to that of a control group ["Meneki Jikken Sosa-ho (Procedures of Immunological Tests)", ed. by Japan Assoc. of Immunol., pages 2267-2276]. The following Table 3 shows the effects of NK374186 on mouse lymphoblast formation.

TABLE 3

| | Effects of NK374186A and B on mouse lymphoblast formation with LPS and Con A | | |
|---|---|---|---|
| Sample | Conc. [μg/ml] | Function index [%] | |
| | | LPS | Con A |
| Control | | 100 | 100 |
| NK374186A | 0.1 | 129.3 | 115.0 |
| | 1 | 107.8 | 117.1 |
| | 10 | 45.3 | 46.7 |
| | 100 | 0.7 | 1.2 |
| NK374186B | 0.1 | 156.3 | 133.7 |
| | 1 | 156.3 | 168.8 |
| | 10 | 94.7 | 111.6 |
| | 100 | 0.8 | 31.5 |

NK374186A and NK374186B promote the lymphoblast formation with LPS and Con A at a lower concentration and, on the contrary, potently suppress the same at a concentration of 10 μg/ml or above.

4. Immunomodulation function of NK374186A an B in transplanted section/host reaction (GVH)

This test is carried out in accordance with the spleen weighing method of Ford et al. [Ford, W. L., et al., Handbook of Experimental Immunology 30 (ed. by Weir, D. M.), Blackwell Scientific Publications, (1978), page 1]. $5 \times 10^6$ spleen cells obtained from a donor C57BL/6 mouse (male, aged 8 weeks) are transplanted into the peritoneal cavity of a BDF mouse (male, aged 7 weeks) which is the F1 hybrid receptor. At the same time, NK374186 and a control drug are dissolved in a solvent (0.25 % gum arabic) and subcutaneously injected into the dorsum of the receptor mouse. As a control, the solvent alone is also subcutaneously injected into the dorsum of the mouse. The same administration is effected on the next day and on the following day. On the seventh day after the transplantation, the spleen of the animal is weighed. Table 4 shows the results.

TABLE 4

| Sample | Effect of NK374186 on transplanted section/host reaction | | |
|---|---|---|---|
| | Dose [mg/kg] | Spleen/total body weight $(\times 10^{-3}) \pm$ S.D. | Index |
| Untreated | | 4.73 ± 0.87 | 1.00 |
| Treated | | 8.03 ± 2.77 | 1.70 |
| 0.25% gum arabic (solvent: control) | | 6.28 ± 2.04 | 1.33 |
| NK374186A | 0.5 | 7.68 ± 2.57 | 1.63 |
| | 5 | 9.67 ± 2.27 | 2.05* |
| | 50 | 10.66 ± 3.14 | 2.26* |
| NK374186B | 0.5 | 8.24 ± 1.54 | 1.74 |
| | 5 | 11.32 ± 3.61 | 2.40* |
| | 50 | 12.63 ± 3.37 | 2.67** |

As the above Table 4 clearly shows, the spleen/total body weight ratio of the NK374186A or NK374186B test group is increased depending on the dose and the GVH reaction is significantly enhanced. Thus it is concluded that the compounds of the present invention have immunopotentiation effects.

5. Function of NK374186 of promoting mouse liver regeneration

In accordance with the method of Higgins and Anderson [Higgins, G. M., et al., Arch. Pathol, 12, 186-202 (1931)], the right diaphragm lobe and the left diaphragm lobe of an ICR mouse (male, aged 6 weeks) are taken out under etherization, thus effecting 70% liver excision. In conducting the suture, 100 mg/kg of NK374186A and NK374186B are intraperitoneally administered. Similarly, a mixture (3.5% DMSO+6.5% Tween 80+90% physiological saline) is administered as a solvent control. Three days after the operation, the regenerated liver is taken out and weighed. Based on the result thus obtained, the liver regeneration ratio is calculated according to the following equation:

$$\text{liver regeneration ratio (\%)} = \frac{A - [B \times C) - D]}{D} \times 100$$

wherein A is the regenerated liver weight,
B is the body weight before excision,
C is the ratio of liver weight to body weight, and
D is the excised liver weight.
Table 5 shows the results.

TABLE 5

| | Function of NK374186A on liver regeneration | |
|---|---|---|
| Compound | Dose (mg/kg) | Liver regeneration ratio (%) ± S.D. |
| Solvent control | | 38.1 ± 2.3 |
| NK374186A | 100 | 51.9 ± 1.3 |

The above results clearly show that NK374186A is effective in promoting the regeneration of liver.

6. Toxicity 100 mg/kg of NK374186A and NK374186B are intraperitoneally administered to CDF-1 mice (male, aged 8 weeks) repetitively once a day for 10 days. Each test compound is administered in the form of a solution in 3.5% DMSO + 6.5% Tween + 90% physiological saline. As a result, none of these compounds causes the death of mice. The clinical conditions of the mice of the test groups show no difference from those of the solvent control group. These results suggest that NK374186A and NK374186B have each a low toxicity.

As the above-mentioned results clearly show, it is expected that the compounds NK374186A, NK374186B, NK374186B3 and NK374186C3 of the present invention are usable as a novel antibacterial agent, a novel antineoplastic, a novel immunomodulator and a novel remedy for hepatic diseases.

To further illustrate the present invention, the following Example will be given. However it is to be understood that the present invention is not restricted thereto but various changes may be made.

EXAMPLE 1

(1) Fermentation 100 ml of a seed culture medium of the following composition was pipetted into a 500-ml Erlenmeyer flask and sterilized in an autoclave at 120° C. for 20 minutes. Next, one platinum loopful of the NK374186 strain (FERM P-12285) (FERM-BP3870) was inoculated thereto and cultured at 27° C. at 200 rpm for 2 days to thereby give the primary seed.

| Composition of seed culture medium: | [%] |
|---|---|
| glucose | 2.0 |
| sucrose | 1.0 |
| lactose | 1.0 |
| glycerol | 0.2 |
| soybean flour (Sun Rich Showa Sangyo K.K.) | 2.0 |
| polypeptone | 0.5 |
| NaNO$_3$ | 0.2 |
| MgSO$_4$ | 0.1 |
| silicone | 0.05 |
| Toho No. 1 | 0.03 |
| tap water | the balance |

In the secondary seed culture, 20 l of the same medium as the one used in the primary seed culture was fed into a 30-l jar fermenter and sterilized. Next, 200 ml of the primary seed obtained above was sterilely transplanted thereto and cultured at 25° C. at 250 rpm while feeding 20 l/min of air for 3 days to thereby give the secondary seed.

In the main culture, 150 l of a production medium, having the same composition as the seed culture medium except that the glycerol concentration was elevated to 1.0%, was fed into a 200-l jar fermenter and sterilized. Next, 2 l of the secondary seed obtained above was sterilely transplanted thereto and cultured at 25° C. at 250 rpm while feeding 150 l/min of air for 4 days. Culture media obtained from 4 jar fermenters were filtered with the use of a filter press to thereby separate the cells from the filtrate.

(2) Purification 200 l of methanol was added to the cells thus obtained and extraction was effected under stirring for 3 hours. Then the cells were separated from the extract by filtration under reduced pressure. The extract thus obtained was mixed with the same amount of water. The mixture was then passed through a 10-l HP-20 column. After washing with 50% methanol, the column was eluted with 20 l of 60% acetone to thereby give a fraction 1. Next, it was eluted with 30 l of 100% methanol to thereby give a fraction 2.

The fraction 1 was concentrated to 4 l under reduced pressure and the pH value was adjusted to 5.0, followed by extraction with ethyl acetate. The extract was concentrated to dryness under reduced pressure. 41 g of the dry product thus obtained was dissolved in ethyl acetate and subjected to silica gel column chromatography. After successively eluting with ethyl acetate a chloroform/methanol mixture (50:1) and a chloroform/methanol mixture (10:1), an active fraction 1a was obtained.

This active fraction 1a was subjected to silica gel column chromatography again and eluted with an ethyl acetate methanol mixture (10:1) to thereby give an active fraction 1b. This active fraction 1b was subjected to LH-20 column chromatography by using methanol as an eluent. Thus 800 mg of NK374186A was obtained.

On the other hand, the fraction 2 was concentrated under reduced pressure to thereby give 28 g of a dry product. This product was then dissolved in chloroform and subjected to silica gel column chromatography. After successively eluting with chloroform, a chloroform/methanol mixture (100:1) and a chloroform/methanol mixture (20:1), active fractions 2a, 2b and 2c were obtained. The active fractions 2a and 2b were subjected to LH-20 column chromatography with the use of methanol as an eluent to thereby respectively give 2.0 g of NK374186B and 1.0 g of NK374186B3. The active fraction 2c was subjected to silica gel column chromatography. After successively eluting with a chloroform/methanol mixture (100:1) and a chloroform/methanol mixture (20:1), the obtained active fraction was subjected to LH-20 column chromatography to thereby give 430 mg of NK374186C3.

What is claimed is:

1. Novel antibiotics (a) NK374186A, (b) NK374186B. (c) NK374186B3 or (d) NK374186C3 or salts thereof having the following physicochemical properties:
   (a) antibiotic NK374186A
      1) appearance: colorless powder,
      3) molecular weight: FD-MS m/z (M+ 735),
      3) rational formula: $C_{34}H_{61}N_3O_{12}S$,
      4) solubility: soluble in lower alcohols, chloroform and ethyl acetate,
      5) Rf value in silica gel thin layer (Art.5715, a product of Merck) chromatography: 0.12 with the use of a chloroform/methanol mixture (20:1) as developer,
      6) UV absorption spectrum: refer to FIG. 1,
      7) IR absorption spectrum: refer to FIG. 2 (determined by using potassium bromide tablet), 8) proton NMR spectrum: refer to FIG. 3 (determined in heavy DMSO),
9) carbon NMR spectrum: refer to FIG. 4 (determined in heavy DMSO), and
10) color reaction: positive in phosphomolybdic acid/sulfuric acid reaction and Tolidine-Chlorine reaction and negative in ninhydrin reaction;

(b) antibiotic NK374186B
1) appearance: colorless powder,
2) molecular weight: FD-MS m/z (M+655),
3) rational formula: $C_{34}H_{61}N_3O_9$,
4) solubility: soluble in lower alcohols, chloroform and ethyl acetate,
5) Rf value in silica gel thin layer (Art.5715, a product of Merck) chromatography: 0.35 with the use of a chloroform/methanol mixture (20:1) as developer,
6) UV absorption spectrum: refer to FIG. 5,
7) IR absorption spectrum: refer to FIG. 6 (determined by using potassium bromide tablet),
8) proton NMR spectrum: refer to FIG. 7 (determined in heavy DMSO),
9) carbon NMR spectrum: refer to FIG. 8 (determined in heavy DMSO), and
10) color reaction: positive in phosphomolybdic acid/sulfuric acid reaction and Tolidine-Chlorine reaction and negative in ninhydrin reaction;

(c) antibiotic NK374186B3
1) appearance: colorless powder,
2) molecular weight: FD-MS m/z (M+ 655),
3) rational formula: $C_{34}H_{61}N_3O_9$,
4) solubility: soluble in lower alcohols, chloroform and ethyl acetate,
5) Rf value in silica gel thin layer chromatography: 0.49 with the use of a chloroform/methanol mixture (20:1) as developer,
6) UV absorption spectrum: refer to FIG. 9,
7) IR absorption spectrum: refer to FIG. 10 (determined by using potassium bromide tablet),
8) proton NMR spectrum: refer to FIG. 11 (determined in heavy DMSO),
9) carbon NMR spectrum: refer to FIG. 12 (determined in heavy DMSO), and
10) color reaction: positive in phosphomolybdic acid/sulfuric acid reaction and Tolidine-Chlorine reaction and negative in ninhydrin reaction;

(d) antibiotic NK374186C3
1) appearance: colorless powder,
2) molecular weight: FD-MS m/z (M+597),
3) rational formula: $C_{34}H_{59}N_3O_7$,
4) solubility: soluble in lower alcohols, chloroform and ethyl acetate,
5) Rf value in silica gel thin layer chromatography: 0.33 with the use of a chloroform/methanol mixture (20:1) as developer,
6) IR absorption spectrum: refer to FIG. 14,
7) proton NMR spectrum: refer to FIG. 15
8) proton NMR spectrum: refer to FIG. 15 (determined in heavy DMSO),
9) carbon NMR spectrum: refer to FIG. 16 (determined in heavy DMSO), and
10) color reaction: positive in phosphomolybdic acid/sulfuric acid reaction and Tolidine-Chlorine reaction and negative in ninhydrin reaction.

2. A process for producing antibiotics NK374186A, NK374186B, NK374186B3 or NK374186C3 or salts thereof as defined in claim 1, which comprises culturing Penicillium sp. NK374186 capable of producing the antibiotics NK374186A, NK374186B, NK374186B3 or NK374186C3 in an enriched medium to thereby form these antibiotics in an amount effective for their isolation, and isolating the antibiotics thus formed from the culture medium.

3. A pharmacological composition which comprises an effective amount of an antibiotic selected from the group consisting of antibiotics NK374186A, NK374186B, NK374186B3 and NK374186C3 as defined in claim 1 together with pharmacological additives.

4. A process for immunopotentiating a warm-blooded animal which comprises administering an effective dose of an antibiotic NK374186A or an antibiotic NK374186B or a salt thereof as defined in claim 1 to the warm-blooded animal.

5. A process for promoting the growth of hepatic cells of a warm-blooded animal with damaged liver which comprises administering an effective dose of an antibiotic NK374186A or a salt thereof as defined in claim 1 to the warm-blooded animal.

* * * * *